US007569212B2

(12) United States Patent
Wagenaar

(10) Patent No.: US 7,569,212 B2
(45) Date of Patent: Aug. 4, 2009

(54) PROCEDURE AND COMPOSITION OF TREATMENT AND/OR CARE OF THE EYE

(76) Inventor: Louis Johan Wagenaar, Joop den Uyllaan 3, Leiden (NL) NL-2314 GC ( * ) Notice: Subject to any disclaimer, the term of this patent is extended or adjusted under 35 U.S.C. 154(b) by 0 days.

(21) Appl. No.: 10/615,592

(22) Filed: Jul. 8, 2003

(65) Prior Publication Data

US 2004/0057980 A1 Mar. 25, 2004

Related U.S. Application Data

(63) Continuation of application No. PCT/NL02/00012, filed on Jan. 9, 2002.

(30) Foreign Application Priority Data

Jan. 9, 2001 (NL) .................... 1017060

(51) Int. Cl.
*A61K 31/74* (2006.01)
*A61F 2/14* (2006.01)
(52) U.S. Cl. ............... 424/78.04; 424/427; 424/429
(58) Field of Classification Search ............... 424/427, 424/429, 78.04
See application file for complete search history.

(56) References Cited

U.S. PATENT DOCUMENTS

| 5,091,421 | A | | 2/1992 | Clark et al. | |
|---|---|---|---|---|---|
| 6,106,828 | A | * | 8/2000 | Bisgard-Frantzen et al. | 424/94.1 |
| 6,136,850 | A | * | 10/2000 | Park et al. | 514/458 |
| 6,281,192 | B1 | * | 8/2001 | Leahy et al. | 514/8 |
| 6,482,799 | B1 | * | 11/2002 | Tuse et al. | 514/14 |
| 7,135,442 | B2 | * | 11/2006 | Schwind et al. | 510/112 |
| 2002/0155961 | A1 | * | 10/2002 | Schwind et al. | 510/112 |
| 2003/0190258 | A1 | | 10/2003 | Smith | |

FOREIGN PATENT DOCUMENTS

| DE | 24 26 757 | | 12/1975 |
|---|---|---|---|
| EP | 0473159 A1 | * | 3/1992 |
| EP | 01100764.8 | * | 1/2001 |
| EP | 1347787 B1 | | 4/2005 |
| RU | 2 055 555 | | 3/1996 |
| SU | 1377104 | | 2/1988 |
| WO | WO 98/32421 | * | 7/1998 |
| WO | WO 02/055118 | | 7/2002 |
| WO | WO 02/062260 | | 8/2002 |

OTHER PUBLICATIONS

"Clinical Study of the Effectiveness of a Dexpanthenol Containing Artificial Tears Solution (Siccaprotect) in Treatment of Dry Eyes," Klin Monatsbl Augenheilkd, 209(2-3):84-88 (1996) in German with English Abstract.
Opposition against EP1347787 filed by Novartis, AG, filed Jan. 13, 2006 (submitted to provide English-language explanation of relevance, if any, of the following German-language references).
Fachinformation ("Technical Information") Siccaprotect*, Ursapharm Arzneimittel GmbH, Jan. 1990. Full English translation attached.
"Producta Ophthalmica Sterilisata," Ursapharm, Jan. 1988. Partial translation English of p. 4 attached.
"Siccaprotect*," Ursapharm Arzneimittel GmbH & Co. KG, Sep. 2000, Full English tanslation attached.
Fachinformation zur Substanzgruppe Kuenstliche Traenen ("Technical information on Artificial Tear Substances"), including Datasheet for Siccaprotect® Augentropfen ("Eye drops"), allegedly available commerically since 1984. English translation of Siccaprotect datasheet attached.
Ophthalmike, 4$^{th}$ edition, pp. 185-186 (1990). English translation of "Dexpantheol" entry spanning pp. 185-186 attached.
Ophthalmike, 4$^{th}$ edition, pp. 509-518 (1990). English translation of Section 3.10.3 Wechselwirkungen zwischen Kontaktlinsen, Kontaktlinsenpflegemitteln und Arzneimitteln ("Interaction between Contact Lenses, Contact-Lens Cleaners and Medications") pp. 513-514 attached.

* cited by examiner

*Primary Examiner*—Carlos A. Azpuru
(74) *Attorney, Agent, or Firm*—Scott E. Kamholz; Foley Hoag LLP

(57) ABSTRACT

A procedure for the manufacture of contact lenses for eye treatment, eye protection and eye-care wherein the lenses are impregnated with a suitable composition, a composition for the impregnation of a contact lens for the treatment and/or care and/or protection of the eye, and a kit containing such a composition and one or more contact lenses are disclosed herein. A method for the treatment and/or car and/or protection of the eye comprising wearing contact lenses impregnated with a suitable composition and a composition for disinfection and/or conservation of eye care products is also disclosed herein.

28 Claims, No Drawings

PROCEDURE AND COMPOSITION OF TREATMENT AND/OR CARE OF THE EYE

RELATED APPLICATIONS

The present application is a continuation of International PCT Application No. PCT/NL02/00012, filed Jan. 9, 2002, which is incorporated herein by reference.

BACKGROUND

The current invention provides a procedure for the manufacture of contact lenses for eye treatment, eye protection and/or eye-care. The invention also provides a composition for the impregnation of a contact lens for the treatment and/or care and/or protection of the eye, a kit containing such a composition and one or more contact lenses as well as contact lenses impregnated with the composition.

Because they regularly have unusual objects in their eyes for years contact lens wearers have a higher chance of damaging their cornea, eye-stratum, the endothelium or other parts of the eyes than non-wearers, for example because chemical substances which may cause irritation or damage to the eye could be released from the lens or the surface of the lens after inserting the lens into the eyes. Lenses which have not been properly cleaned or damaged lenses as well as dust-particles, traces of sand or pollen which have gotten under the lens could also affect the cornea. These damages or irritations can be superficial and temporary, but could also result in far-reaching consequences since lenses are usually worn daily. Health risks could occur, varying from irritated and red eyes to serious complications such as permanent damage of the cornea resulting in blindness.

The cause of such complications is multifarious. Placing the contact lens onto the eye disturbs its physiological condition. After habituation a new balance will be reached that can be disturbed again by various factors, such as ageing of the contact lens, damage to and deposit on the lens, change of tear-flow with respect to composition and quantity due to frequency and manner of winking, chemical toxicity of substances the user is in contact with, mechanical pressure and chronic lack of oxygen. The ageing of the user may bring about changes in his or her eyes thereby disturbing the physiological balance. The use of medication or the development of allergies may also lead to irritations or damage of parts of the eyes.

Because nowadays contact lenses are frequently used for longer periods of time careful and regular cleaning has become more important. If this is not done sufficiently, bacteria, proteins etc., for instance, may cause irritations and damage more promptly. To prevent permanent damage it is vital that possible damage to the cornea or other parts of the eyes is treated as soon as possible.

Moreover, contact lens wearers may need extra protection for their eyes. It could be useful to the eyes to dispense extra nutrition, such as vitamins and provitamins or, additionally, those substances which offer protection or allow, support or accelerate the repair of an occurring damage. In eye health-care several products are known to assist in the accelerated recovery of the soundness of the cornea. These products, however, usually have to be administered (dripped in or applied onto the eye) separately or have to be swallowed by the user.

SUMMARY

It is the aim of the current invention to provide the opportunity for a long-term care or treatment and/or protection and/or care of the eyes.

In accordance with one aspect of the present invention, a method for the production of contact lenses for the treatment and/or care and/or protection of the eye may comprise the impregnation of contact lenses in a solution which comprises one or more suitable components for the treatment and/or care and/or protection of the eye.

In accordance with another aspect of the present invention, a composition for the treatment and/or care and/or protection of the eye may comprise at least one suitable component for the treatment and/or care and/or protection of the eye.

In accordance with a further aspect of the present invention, a contact lens for treatment and/or care and/or protection of the eye may be impregnated with a composition comprising at least one suitable component for the treatment and/or care and/or protection of the eye.

DETAILED DESCRIPTION

Considering the possibilities of irritation and damage to the cornea, the stratum, the endothelium or other parts of the eyes are manifold, one requires protection, conditioning and whenever possible, restoration of the sustained damage to the eye. The current invention therefore provides a method for the manufacture of contact lenses for the treatment and/or care and/or protection of the eyes, comprising the impregnation of contact lenses in a solution which contains suitable compounds for the treatment and/or care and/or protection of the eyes. By wearing contact lenses the compounds which treat and/or protect and/or care of the eyes will be in contact with part of the eyes. This way the lens will be a method of administering these compounds which will often imply a more long-lasting administering compared to current eye-drops. The compounds mentioned can be either absorbed into the lens material or be attached to them or both. The term 'impregnate' in this application refers to either of these or to a combination of both.

Furthermore the current invention provides a composition for the impregnation of contact lenses for the treatment and/or care and/or protection of the eyes, comprising compounds suitable for eye treatment or care or protection.

The current invention offers various types of compounds dependent on the type of treatment, care or protection required. For the benefit of the user these compositions can be combined with the compounds usually used for disinfecting, cleaning, insertion, moisturizing, rinsing or storing of contact lenses, so that the user need not add these compounds separately. However, it is likewise possible to just impregnate the lenses with the above-mentioned care or treatment products to prevent damage caused by other cleaning-agents or disinfectants.

Compounds that can be applied, but are not limited to substances which feed or treat the eye or may improve, accelerate or initiate local damage repair, or helps to avoid local damage or irritations of parts of the eye, are: for instance dexpanthenol, pantothenic acid, hyaluron acid, retinol (Vitamin A) and retinyl derivatives, carotene, thiamine (Vitamin B1), riboflavine (Vitamin B2), pyridoxine (Vitamin B6), nicotinic acid, nicotine acidamin, biotine (Vitamin B7), niacinamide and niacine (vitamin B3), ascorbic acid (Vitamin C) and other anti-oxidants, saccharose, honey and other bee products, red beetroot syrup, collagen, gelatin, taurin, serine protease and other enzymes, propamidines, Vitamin D and its derivatives such as calciferol, Vitamin K, tannin, pyruates, fibroplastin, fibronectine and fibrohydrolysate, heparin, alfa-ketaglutarine acid, carnisin, laminisin, mucin, tenascin, peptides epidermal growth factor (EGF), platelet-derived growth factor (PDGF), fibroblast growth factor (FGF) and all ophthalmologically acceptable salts and derivatives of the compounds mentioned above, selenium, calcium, zinc and other minerals.

Products used for maintenance and storage of contact lenses, like cleaning products and disinfecting solutions, and sprays, so-called all-in-one solutions, storage liquids and rinsing liquids, insertion solutions and moisturizers, neutralizers in either liquid or tablet form, gels, coatings and tablets which either make or assist in making contact lens solutions or make solutions come into being or are used for or in such solutions.

According to the current invention the composition can therefore appear in various forms, such as a solution, spray or tablet which after dissolution makes a solution. Compounds intended for the care of contact lenses may also be part of a tablet which is combined with a solution that contains the care, treatment or protection agent or the reverse. Obviously both could also be included in one tablet or in separate tablets. Even so compounds can be included in a solution that is to be mixed with a solution without a compound.

Since the current substances which necessarily have to be applied for their germicidal and preservative effects in eye-care solutions, eye-drops and contact lens care solutions and which are germicidal in a short period of time and sufficiently limiting increase in germ population usually have the disadvantage of causing irritation or even attacking the eye to a large or lesser degree it would be greatly advantageous to use compounds in eyecare solutions, eye-drops and contact lens solutions for germicidal or conservation purposes which are non-irritant or protect against these irritations or damages. Possible damage and irritation of the cornea or other parts of the eye will thus be avoided. An additional aim of the current invention is to disclose a method for improvement of the way a desired (and often necessary) antibacterial effect of a composition for contact lens care or eye-care/eye-drops can be reached. A number of peptides are naturally found in the eye. They have a protective effect on the eye and particularly the cornea. The use of peptides in a composition for use in a contact lens solution, but also in eye-drops, could be greatly advantageous, because many peptides do not cause damage to the cornea; to some extent they also offer protection. They also offer protection from and support against bacterial infections, especially for people prone to such infections or people whose corneas are easily damaged.

According to the current invention peptides can be used separately or in combination with other eye-care products or treatments.

The composition according to the current invention can be applied when impregnating all kinds of contact lenses, especially and preferably soft lenses, but also hard lenses, disposable lenses and long-lasting ones as well as extended wear lenses and intra-ocular lenses would benefit. Impregnation can be carried out by the user, for instance during maintenance, but also, as with new lenses, in the delivery packaging.

It is not necessary for the user using the contact lenses according to the current invention to be already familiar with wearing lenses. People, and even animals, who in fact do not need any eye-correction, but who require for instance certain nutrients for the eye or products to possibly initiate, support or accelerate healing sores or injuries could wear contact lenses or similar objects according to the current invention on or in the eye to facilitate the required compound(s) on or into the eye. It is not necessary for the active component with which contact lenses have been impregnated to repair or prevent any damage. Also medicines can be administered through a contact lens according to the current invention. An example of another type of effective compound, in this case a medicine, which could be administered advantageously to the eye according to the current invention is for instance cromoglycate. This compound works as a precautionary protection against allergies. A contact lens with this compound could be used when the user expects an allergic reaction, for example in a period with high levels of pollen. Other compounds can be used as well to either prevent or reduce allergic reactions, such s emedastine, azelastine and nedocromil.

Other applications of contact lenses according to the current invention could be found in the treatment of so-called 'dry eyes' or irritated or red eyes, hence called 'dry eyes'. Currently mainly eye-drops are used to treat this. Such eye-drops, however, usually offer only short-term relief. In order to lengthen the availability of the active agents for the treatment of the eyes several complex or expensive possibilities for slow-release eye-drops have been proposed. The contact lenses according to the current invention offer a simple, cheap and elegant alternative.

It could be particularly advantageous to use the compounds suggested in the current invention as giving relief to dry eyes in combination with polymers from which is known or believed that they, when used in eye-drops, offer relief, such as polymers of the type polyvinylpyrrolidone(PVP), polyvinyl alcohol (PVA), hydroxypropyl methylcellulose (HPMC), hydroxy propyl cellulose (HPC), Carbomere or Dextrane. Other substances that may be combined with the compounds include polyhexamethylene biguanide hydrochloride (PHMB HCl), boric acid, borax, sodium chloride (NaCl), and ethylenediamine tetraacetic acid (EDTA).

As mentioned above contact lenses according to the current invention can also be used to apply substances which cure or correct eye-diseases or disorders and which should be administered once or several times a day to take sufficient effect at least part of the day. The use of contact lenses according to the current invention could be effective here. Moreover, the use of contact lenses will generally result in a more constant level of the effective agent at the point of application than would have been possible with the use of eye-drops or even eye-balm. Eye-balm also has the disadvantages of causing limited eye-sight directly after application and a less easy way of application for some users compared to applying contact lenses. For wearers of contact lenses the use of the current invention with their own lenses is particularly economical, because they do not need to perform any supplementary actions.

An advantage of the current invention is that the price of contact lenses has dropped considerably over the last few years especially that of short-term use lenses such as the so-called day-lenses, week-lenses, month-lenses or three-months'-lenses. Such lenses are a preferable embodiment of the current invention.

The current invention will be illustrated in the following examples:

EXAMPLES

Examples of compositions to be used in the procedure according to the current invention are the following:

A. All-in-One Solutions:
1. PHMB HCl 2.5 ppm
2. Boric Acid 0.75%
3. Borax 0.15%
4. NaCl 0.40%
5. EDTA-Na 0.03%
6. HPMC 10,000 0.10%
7. Dexpanthenol 1.0%
8. pH adaptation with NaOH or HCl to pH 7.4

B. Neutralizers (Tablets):
1. Catalase 3000 IU
2. KH2PO4 50 mg
3. K2hPO4 150 mg
4. NaCl q.s.
5. Na-EDTA 0.2 mg
6. Collagene 5 mg
7. PVP K 90 10 mg C. Storage Solutions and Insertion Solutions:
1. HPMC 4000 cP 0.2%
2. Citric Acid 0.5%
3. Na citrate 1.0%
4. NaCl ad 300 mOsm
5. Na-EDTA 0.02%
6. Alexidine 2 HCL 0.5 ppm
7. Hyaluronic Acid 0.25%
8. pH adaptation with NaOH or HCL ad pH 7.2

The invention claimed is:

1. A method for impregnating a soft contact lens, comprising impregnating said soft contact lens with a solution while the contact lens is not contacting an eye, wherein the solution comprises dexpanthenol.

2. A kit for contact lenses comprising:
one or more soft contact lenses, and
a composition comprising dexpanthenol, or ophthalmologically acceptable salts thereof, wherein said composition is ophthalmologically acceptable;
wherein:
(a) the composition comprises one or more peptides as a component to disinfect, protect, clean and/or store the contact lens; or
(b) said composition further comprises one or more of: HPC and HPMC; or
(c) the kit further comprises one or more of: cromoglycin acid, Edamastine, azelastine and nedrocromil and their ophthalmologically acceptable salts and derivatives.

3. The kit of claim 2, wherein the composition further comprises compounds to disinfect, clean, insert and/or store contact lenses.

4. The kit of claim 2, wherein the composition comprises one or more peptides as a component to disinfect, protect, clean and/or store the contact lens.

5. The kit of claim 2, further comprising one or more of: cromoglycin acid, Edamastine, azelastine and nedrocromil and their ophthalmologically acceptable salts and derivatives.

6. The kit of claim 2, wherein the composition takes the form of a spray, solution, gel, coating and/or tablet.

7. The kit of claim 6, wherein said contact lens is impregnated with said solution.

8. The kit of claim 2, wherein said contact lens is a day lens.

9. The kit of claim 2, wherein said composition comprises at least 1% dexpanthenol by weight.

10. The kit of claim 2, wherein said composition further comprises one or more components selected from the group consisting of polyvinylpyrrolidone (PVP), polyvinyl alcohol (PVA), hydroxypropyl methylcellulose (HPMC), hydroxy propyl cellulose (HPC), carbomere, and dextrane.

11. The kit of claim 2, wherein said composition further comprises one or more of: HPC and HPMC.

12. The method of claim 1, wherein said contact lens is a day lens.

13. A method of disinfecting and/or storing a soft contact lens, comprising placing said soft contact lens into a solution comprising dexpanthenol.

14. A method of cleaning a soft contact lens, comprising rinsing said soft contact lens with a solution comprising dexpanthenol.

15. The method of claim 14, wherein the solution further comprises at least one of PVP, PVA, HPMC, HPC, carbomere, and dextrane.

16. The method of claim 15, wherein the solution further comprises at least one of HPMC and HPC.

17. The method of claim 15, wherein the solution further comprises at least one of sodium chloride (NaCl), polyhexamethylene biguanide (PHMB), and ethylenediamine tetraacetic acid (EDTA).

18. The method of claim 17, wherein the solution further comprises NaCl, PHMB, and EDTA.

19. The method of claim 15, wherein the solution further comprises at least one of PVP and PVA.

20. The method of claim 14, wherein the solution comprises:
(a) PHMB HCl 2.5 ppm;
(b) Boric Acid 0.75%;
(c) Borax 0.15%;
(d) NaCl 0.40%;
(e) EDTA-Na 0.03%;
(f) HPMC 10,000 0.10%; and
(g) Dexpanthenol 1.0%;
wherein the solution is adapted with NaOH or HCl to pH 7.4.

21. The method of claim 13, wherein the solution further comprises at least one of PVP, PVA, HPMC, HPC, carbomere, and dextrane.

22. The method of claim 21, wherein the solution further comprises at least one of HPMC and HPC.

23. The method of claim 21, wherein the solution further comprises at least one of sodium chloride (NaCl), polyhexamethylene biguanide (PHMB), and ethylenediamine tetraacetic acid (EDTA).

24. The method of claim 23, wherein the solution further comprises NaCl, PHMB, and EDTA.

25. The method of claim 21, wherein the solution further comprises at least one of PVP and PVA.

26. The method of claim 13, wherein the solution comprises:
(a) PHMB HCl 2.5 ppm;
(b) Boric Acid 0.75%;
(c) Borax 0.15%;
(d) NaCl 0.40%;
(e) EDTA-Na 0.03%;
(f) HPMC 10,000 0.10%; and
(g) Dexpanthenol 1.0%;
wherein the solution is adapted with NaOH or HCl to pH 7.4.

27. The method of claim 1, wherein the contact lens comprises a soft contact lens.

28. The kit of claim 2, wherein at least one of the one or more contact lenses is stored in the composition.

* * * * *